United States Patent [19]

Dickey

[11] Patent Number: 4,738,062

[45] Date of Patent: Apr. 19, 1988

[54] MULTIPLE HELIX PICKET

[76] Inventor: Charles N. Dickey, 50 Riceville Rd., Apt. C-207, Asheville, N.C. 28805

[21] Appl. No.: 860,630

[22] Filed: May 7, 1986

Related U.S. Application Data

[63] Continuation-in-part of Ser. No. 677,500, Dec. 3, 1984, abandoned.

[51] Int. Cl.$^4$ .............................................. E02D 5/74
[52] U.S. Cl. ...................................... 52/157; 433/173
[58] Field of Search ................... 52/155, 157; 433/173

[56] References Cited

U.S. PATENT DOCUMENTS

| | | | |
|---|---|---|---|
| 273,887 | 3/1883 | Petrequin | 52/157 |
| 535,239 | 3/1895 | Douglass | 52/157 |
| 815,588 | 3/1906 | Hile et al. | |
| 907,799 | 12/1908 | Hawley | 52/157 |
| 930,792 | 8/1909 | Perry | |
| 1,800,504 | 4/1931 | Chance | 52/157 |
| 1,850,868 | 3/1932 | Drake | 52/155 X |
| 2,653,688 | 9/1953 | Gordon | |
| 4,162,789 | 7/1979 | Hollaway | 52/157 X |

OTHER PUBLICATIONS

"Maxillary Fixed Prostheses on Osseointegrated Dental Implants", by Lundqvist & Carlsson, (Aug. 1983–vol. 50, No. 2) 9 Pages.

Primary Examiner—J. Karl Bell
Attorney, Agent, or Firm—Harness, Dickey & Pierce

[57] ABSTRACT

A picket for anchoring objects to an article is disclosed. The picket includes multiple helically-shaped members disposed about a common longitudinal axis and connected to one another. In one embodiment the object sought to be secured is placed between the end portions of the helically-shaped members and the picket is rotated into engagement with the surface thereby trapping the object sought to be secured between the helically-shaped members and a connecting means. The multiple helically shaped members increase the surface engaging force and permit the object sought to be anchored to be placed in a desired location on a surface and anchored without requiring the use of additional connecting means. In other embodiments an anchoring portion of the picket is integrally formed with, or fixed to, a generally cylindrical collar portion to provide both secure anchoring and lateral stability. A dental application for anchoring a dental prosthesis to a bone structure is also disclosed.

17 Claims, 3 Drawing Sheets

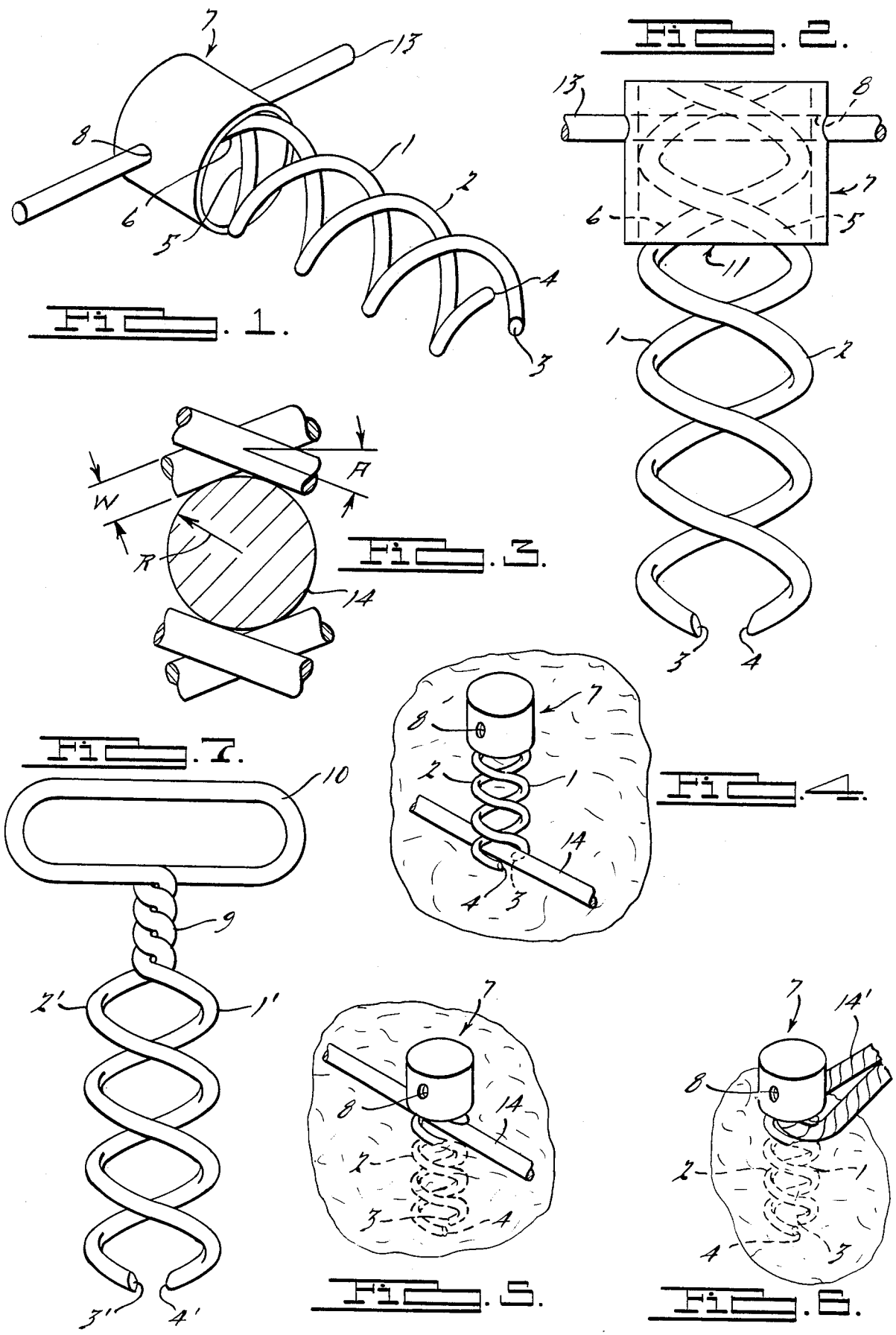

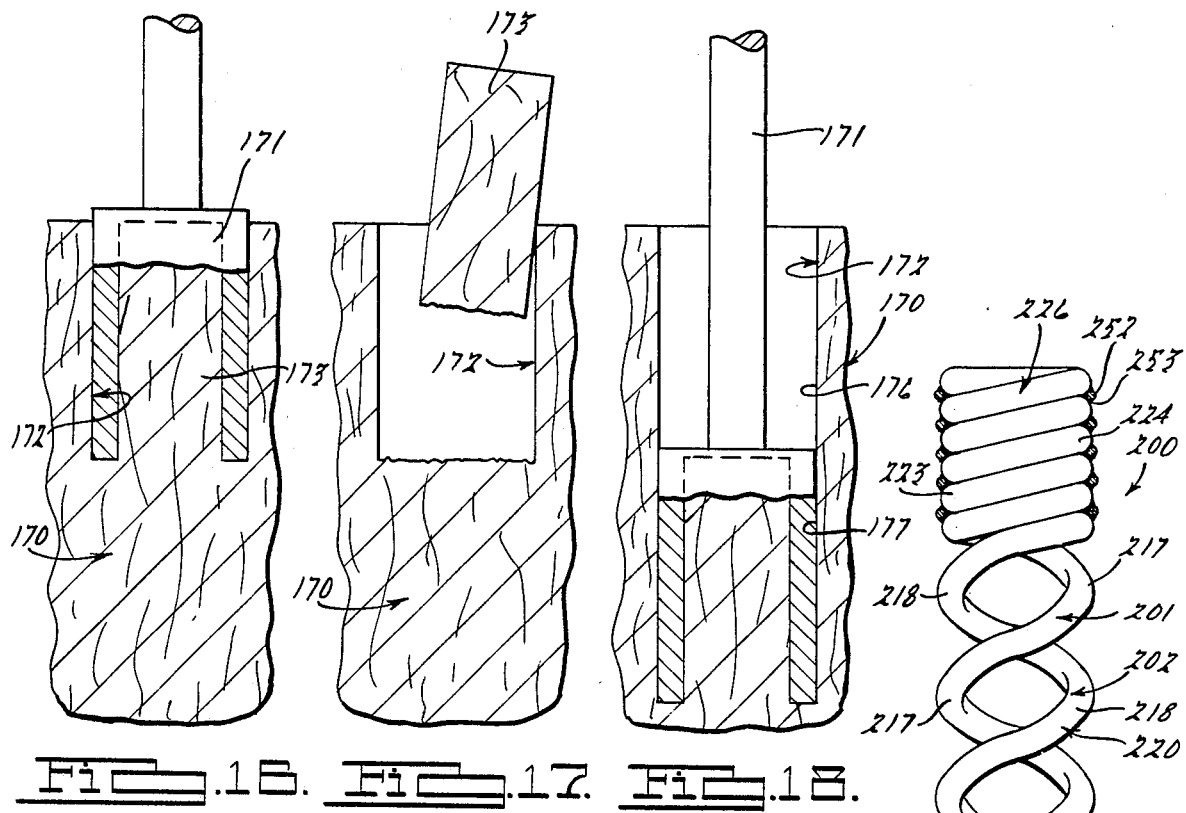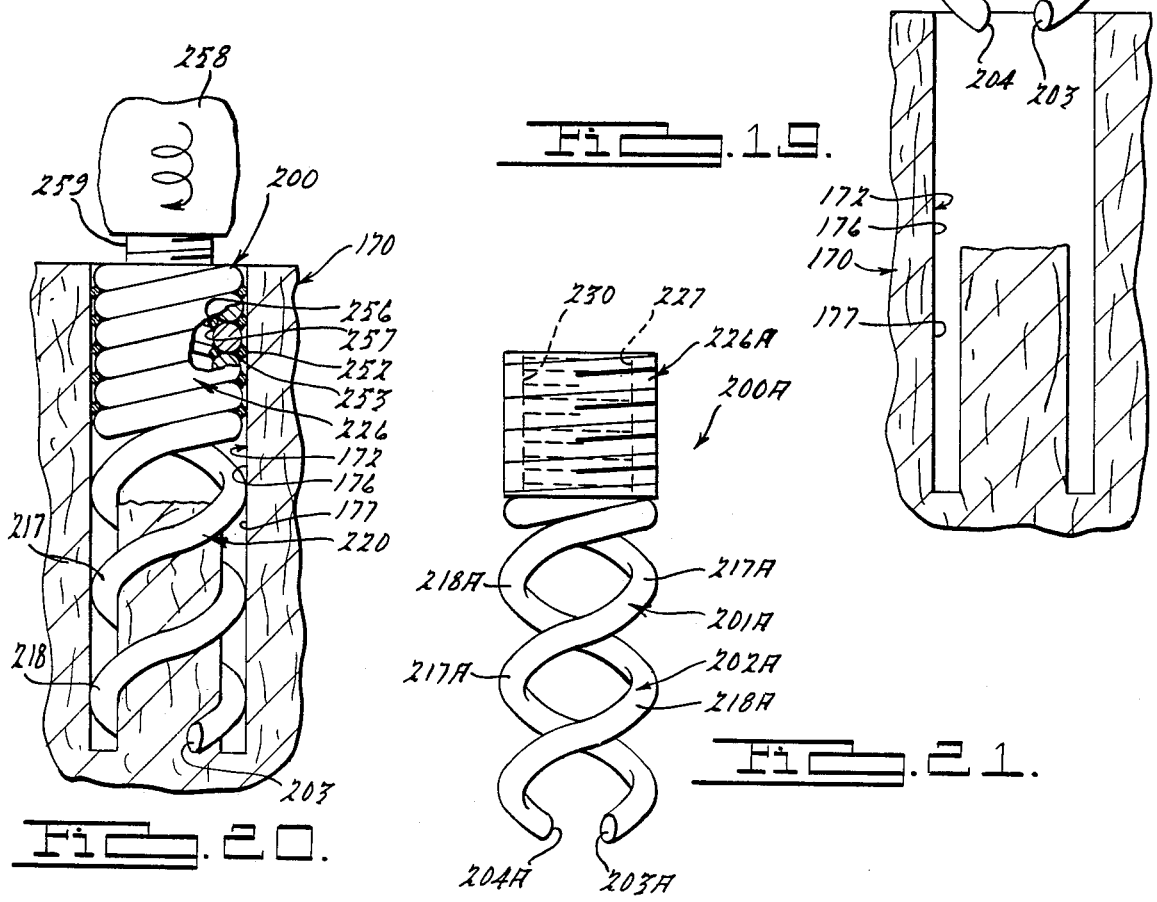

MULTIPLE HELIX PICKET

BACKGROUND AND SUMMARY OF THE INVENTION

This is a continuation-in-part of a copending application, Ser. No. 677,500, filed Dec. 3, 1984, now abandoned the disclosure of which is incorporated by reference herein.

The present invention relates to pickets for use in anchoring objects to articles and is more particularly directed to helically shaped pickets which may be installed or removed by a rotary motion. In addition, some embodiments of the present invention relate to a dental application for anchoring a dental prosthesis to a bone structure.

Helically shaped pickets have been devised in the past for anchoring objects, such as those shown in U.S. Pat. Nos. 2,653,688; 930,792; and 815,588; however, these prior designs cannot be placed over an object to be anchored which is already in position and used to anchor same without any additional connection. Furthermore, these and other pickets known in the prior art do not provide sufficient flexibility of application or lateral stability required in many instances, and are generally not suitable for the dental prosthesis application discussed herein in connection with the present invention.

In one embodiment of the present invention, the object sought to be anchored can be placed in its final desired location upon a surface of another article prior to installation of the picket. Installation is realized by rotating the picket into engagement with the surface of the article. Installation is complete when the top of the picket engages the object to be anchored. No additional connections are required. No further adjustment of the location of the object sought to be anchored is required. The picket of the present invention may be removed by reversing the direction of rotation used during installation.

In addition, the present invention improves upon prior designs by providing multiple surface engaging helices which effectively increases the holding force of the picket.

According to another embodiment of the present invention, a picket for anchoring an object to an article includes two helical members disposed concentrically about, and spaced radially from, a longitudinal axis. An anchoring portion of the picket includes adjacent bights of the helical members spaced longitudinally from one another, and a generally cylindrical collar portion of the picket is adapted for engagement with the article being anchored.

The above-mentioned cylindrical collar portion can be fixed to the anchoring portion, or can be formed integrally from a portion of the two helical members having their longitudinally adjacent bights engaging one another.

The present invention also finds applicability in anchoring a dental prosthesis to a jaw bone structure. The picket is received in an opening, or socket, in the bone structure, with the above-mentioned anchoring portion being threadably inserted in threaded engagement with the bone structure adjacent the socket. The dental prosthesis is secured to the above-mentioned collar, which can be equipped with either internal or external threads. The bone readily grows together between the open, or generally longitudinally spaced, bights of the anchoring portion to securely fix the picket, and thus the dental prosthesis, to the bone structure.

In order to avoid adversely affecting the bone structure, and to withstand the dental application, the above-mentioned dental anchoring picket is preferably composed of titanium, or a titanium-bearing material. In such an embodiment, the internal or external threads can be formed by heliarc welding, laser welding, or other suitable fusion of a thin helical rod to the inside or outside of the collar portion.

Additional objects and advantages of the present invention will become apparent from a reading of the detailed description of the preferred embodiments and the appended claims by reference to the accompanying drawings.

BRIEF DESCRIPTION OF THE DRAWINGS

FIG. 1 is a perspective view of a picket embodying the principles of the present invention.

FIG. 2 is a side view of the picket of FIG. 1.

FIG. 3 is an enlarged vertical section illustrating a cylindrical object to be anchored.

FIG. 4 is a perspective view of the picket of FIG. 1 in a pre-installation position above a cylindrical object sought to be anchored to the ground.

FIG. 5 is a perspective view of the picket of FIG. 1 installed and anchoring a cylindrical object to the ground.

FIG. 6 is the picket of FIG. 1 shown anchoring a rope or line.

FIG. 7 is a side view of a second embodiment of the present invention.

FIG. 15 is an exemplary, enlarged fragmentary view illustrating the formation of threads by the securement of a thin helical rod either to the exterior of the collar portion shown in FIG. 13, or to the interior of the collar portion shown in FIG. 14.

FIG. 16 is a diagrammatic representation of one of the steps involved in a dental application for the present invention, wherein a drilling tool is used to form an opening in a bone structure, to accommodate a snug fitting anchoring picket without bone damage.

FIG. 17 illustrates the removal of the bone structure core formed by the drilling tool of FIG. 16, in order to form a generally cylindrical opening in the bone structure.

FIG. 18 illustrates the use of the drilling tool of FIG. 16 to form an annular cylindrical inner portion of the opening in the bone structure.

FIG. 19 illustrates the insertion of a picket according to the present invention into the opening in the bone structure for purposes of anchoring a dental prosthesis thereto.

FIG. 20 illustrates the securement of the picket of FIG. 19 to the bone structure, with the anchor portion of the picket threadably engaging the bone structure adjacent the annular cylindrical inner portion of the opening, as well as illustrating the threaded attachment of the dental prosthesis to the anchor.

FIG. 21 illustrates an alternate embodiment of the dental prosthesis anchoring picket used in connection with the prosthesis anchoring operation illustrated in FIGS. 16 through 20.

DETAILED DESCRIPTION OF THE PREFERRED EMBODIMENTS

Figure 8:
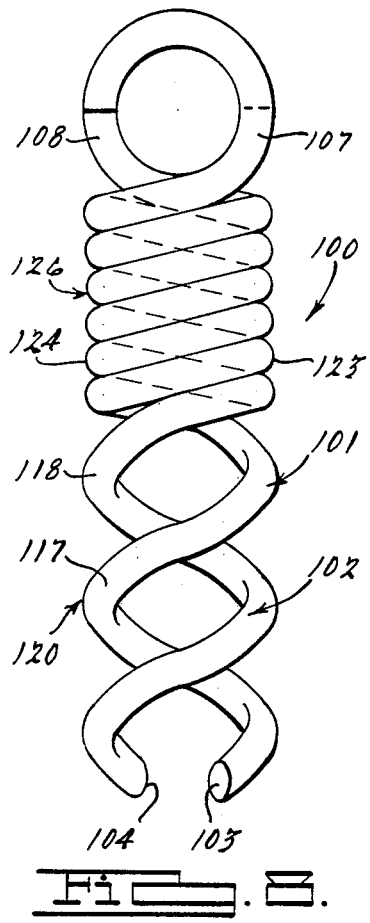
FIG. 8 is a side view of another exemplary picket according to the present invention, having an anchoring portion and a generally cylindrical collar portion, with a hook-like portion on the collar portion being adapted to engage an object to be anchored.

FIGS. 1 through 21 depict various exemplary embodiments of the present invention for purposes of illustrating its wide variety of applications. Such exemplary embodiments are depicted and described herein for purposes of illustration only, since one skilled in the art will readily recognize from the following description and claims, as well as the accompanying drawings, that the present invention is equally applicable to anchoring pickets and anchoring applications other than those illustrated by the exemplary embodiments shown in the drawings.

Referring now to the drawings, wherein FIGS. 1 through 6 illustrate one exemplary embodiment of the invention, a picket comprises a pair of helically shaped members 1 and 2, the free ends of which are tapered, as indicated at reference numerals 3 and 4 respectively, and the opposite ends of which are attached to a connecting means 7. The helically shaped members 1 and 2 may be constructed by forming a heavy wire or rod about a mandrel which has been configured to produce the desired shape, and may be attached to a connecting means 7 such as by welding, as indicated at reference numerals 5 and 6. The connecting means 7 may be constructed from a simple section of pipe having an inside diameter substantially equal to the outside diameter of the helically shaped members 1 and 2, and has a holding surface 11 adapted to engage the object to be anchored. The connecting means 7 includes an opening 8 into which a handle 13 may be inserted to increase the effective torque applied about the axis of the picket.

The pitch angle and the diameter of the helically shaped members 1 and 2 must be selected so that the "through" opening between adjacent coils of both helically shaped members 1 and 2 will accommodate an object 14 sought to be anchored. For a picket having two helically shaped members equally distributed about a common axis wherein the helically shaped members have a pitch angle of 30 degrees and are constructed of a wire having diameter W, the minimum helix pitch diameter to be used to secure a generally cylindrical object of radius R may be approximated from the equation:

$$\text{diameter} = \frac{4(R + W)}{Pi}$$

For other pitch angles A, use:

$$\text{diameter} = \frac{2(R + W)}{Pi \sin A}$$

Similar equations may be developed for use in specifying helixes to be used in conjunction with this invention for secring objects having other cross-sectional shapes.

In use, the opening between the tapered end portions 3 and 4 of the helically shaped members 1 and 2 is placed over the object sought to be anchored, as best shown in FIG. 4, and the picket is rotated via the connecting means (using the handle 13 if desired) in a direction which causes the helically shaped members to penetrate the surface. The installation process is completed when the holding surface 11 on the connecting means 7 engages the object 14 sought to be anchored, as best shown in FIG. 5. For removal, the process is reversed.

FIG. 6 shows the picket of FIGS. 1 through 5 being used for anchoring a rope, cable or line 14'. The installation and removal process of the picket remains the same as that shown in FIGS. 1 through 5, regardless of the object being anchored.

In a further embodiment of the invention shown in FIG. 7, the entire picket is formed out of a single piece of material, with a pair of helically shaped members 1' and 2' being tightly twisted together to form a connection portion 9 having an integral loop 10 extending upwardly therefrom to form a handle 10. Construction of this embodiment may be accomplished by forming a wire or rod having sufficient structural characteristics to a mandrel of the desired shape. The handle 10 may be shaped to receive an arm or bar (not shown), which may be used to increase the effective torque applied about the central axis of the picket, or in the alternative may itself have an increased radial dimension to similarly increase the applied torque.

In FIG. 8, another exemplary embodiment of the present invention is shown wherein a picket 100 is formed from a pair of helically shaped members 101 and 102, preferably having tapered ends 103 and 104, respectively, which are similar to the tapered ends 3 and 4 of the picket shown in FIGS. 1 through 6. The opposite ends of the helically shaped member 101 and 102 are formed into generally semi-circular or hook-shaped holding portions 107 and 108, respectively. Such holding portions 107 and 108 are adapted to receive a bar or other torque-applying member for purposes of threadably anchoring the picket 100 into the earth or other article to which an object is to be anchored.

Figure 9:
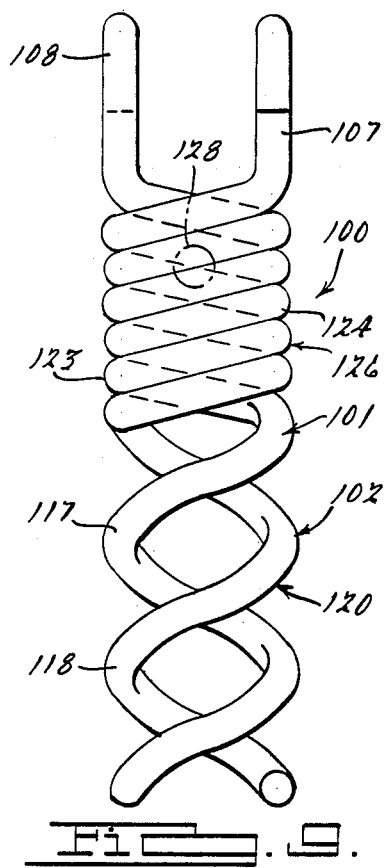
FIG. 9 is a side view of the picket of FIG. 8, but rotated 90 degrees about its longitudinal axis.

The bights 117 and 118 of the helically shaped members 101 and 102, respectively, are longitudinally spaced from one another to define a relatively open anchoring portion 120 of the lower portion of the picket 100, as viewed in FIGS. 8 and 9. In contrast, the bights 123 and 124 of the helically shaped members 101 and 102, respectively, are relatively tightly wound, preferably with longitudinally adjacent bights in engagement with one another, at an upper portion of the picket 100, between the anchoring portion 120 and the holding portions 107 and 108. Such relatively tightly wound bights 123 and 124 of the helically shaped members 101 and 102, respectively, define a generally cylindrical collar portion 126 of the picket 100.

Although both the anchoring portion 120 and the collar portion 126 of the picket 100 shown in FIGS. 8 and 9 both serve to anchor and secure the picket 100 into the earth or other article, the anchoring portion 120 provides the primary resistance to removal of the picket 100 in a longitudinal or outward direction, while the collar portion provides for increased lateral stability and rigidity of the picket 100, thereby providing for a more effective anchor than that of the pickets shown in FIGS. 1 through 7 and discussed above.

Although the picket 100 shown in FIGS. 8 and 9 can be threadably anchored into the earth or other article in a manner similar to that described above in connection with FIGS. 1 through 7, by inserting a bar or other torque-applying member through the holding portions 107 and 108, as discussed above. A torque opening 128 can also optionally be provided in a laterally extending direction through the collar portion 126, if desired in a particular application. Such optional torque opening 128 is adapted to receive a bar or other torque-applying member for threadably rotating the picket 100 in a manner similar to that described above.

Figure 10:
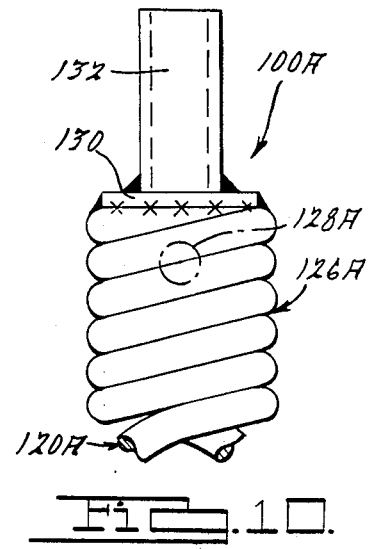
FIG. 10 is a partial side view of another exemplary picket, which is similar to that of FIGS. 8 and 9, but which has a plate secured to the collar portion of the picket and an exemplary object-engaging or object-holding structure secured to the plate in order to anchoringly accommodate a sign post or other object to be anchored.

In FIG. 10, another exemplary embodiment of the present invention is illustrated, wherein a picket 100A is generally similar to the picket 100 described above in connection with FIGS. 8 and 9, except that the holding portions 107 and 108 are deleted and replaced by a plate or other member 130, which is fixedly secured to the collar portion 126A. An object-engaging holder 132 is in turn fixedly secured, such as by welding for example, to the plate 130 and is adapted for secure engagement with an object to be anchored, such as a sign post, flag post, or other object.

Figure 11:
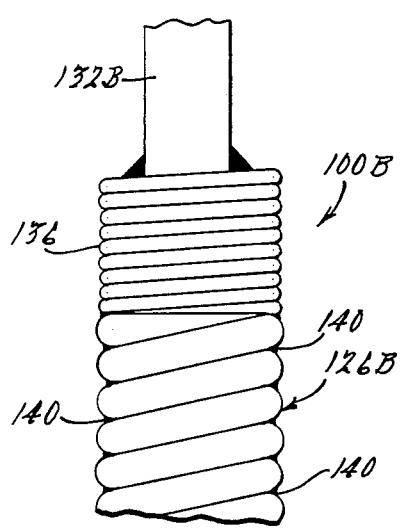
FIG. 11 is a partial side view of still another exemplary picket, similar to that of FIG. 10, but with a deflectable coil spring interposed between the collar portion of the picket and the object-engaging structure.

FIG. 11 illustrates an embodiment of the invention similar to that of FIG. 10, wherein an exemplary picket 100B is generally similar to the picket 100A of FIG. 10, but the plate 130 shown in FIG. 10 is replaced by a laterally deflectable spring 136 between the collar portion 126B and the object-engaging holder 132B. Such coil spring 136 is especially desirable in anchoring applications wherein the object to be anchored is likely to be contacted by other objects, or is susceptible to wind loads imposed thereon. Thus, the anchored object can be displaced from its normal orientation with respect to the picket 100B and will resiliently return to such normal orientation by action of the spring 136.

Optionally, as with any of the embodiments of the present invention, longitudinally adjacent bights of the collar portion 126B can be fixedly secured to one another such as by welding, as indicated for purposes of illustration by reference numeral 140 in FIG. 11.

Figure 12:
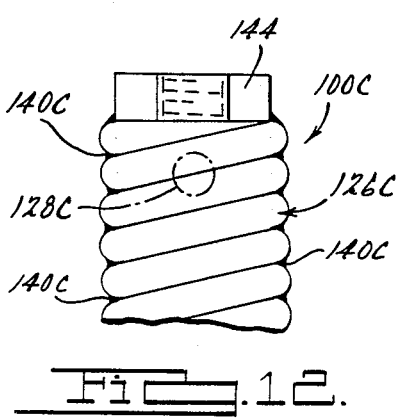
FIG. 12 is a partial side view of another exemplary picket according to the present invention, having a nut or other threaded fastener secured to the collar portion of the picket and adapted for interconnection with an object to be anchored.

In FIG. 12, still another exemplary embodiment of the present invention. Exemplary picket 100C in FIG. 12 is generally similar to the pickets illustrated in FIGS. 8 through 11, except that a nut or other internally or externally threaded fastener 144 is secured to the outer or upper end of the collar portion 126C for threadably attaching and securing an object to the picket 100C.

Figure 13:
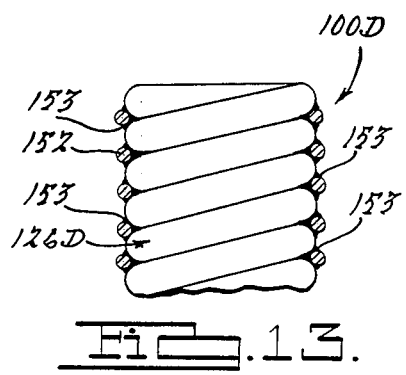
FIG. 13 is a partial side view of the collar portion of still another embodiment of the present invention, with the collar portion having external threads formed by securing a thin helical rod thereon.

In FIG. 13, a collar portion 126D of an exemplary picket 100D has external threads formed thereon for purposes of threadably engaging an internally-threaded object to be anchored. Alternately, such external threads may be provided for purposes of even further enhancing the engagement of the collar portion of the picket 100D with the earth or other article to which an object is to be anchored.

As shown in FIG. 13, such external threads on the collar portion 126D can be formed by the provision of a rod 152 that has a thickness that is thin relative to the thickness of the helical members of the picket, and which is formed in a helical configuration and secured to longitudinally-adjacent bights on the collar portion 126D, such as by welding as indicated by reference numeral 153. Alternately, however, such external threads may be cut or otherwise formed on the exterior of the collar portion 126D in a variety of ways familiar to those skilled in the art (such as with watchmakers' or other precision taps or dies).

Figure 14:
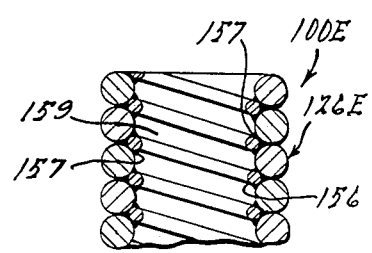
FIG. 14 is a partial longitudinal cross-sectional view of the collar portion of still another exemplary picket according to the present invention, which is similar to that of FIG. 13, but which has internal threads therein.

In FIG. 14, still another exemplary picket 100E is generally similar to the picket 100D in FIG. 13, except that threads are formed on the interior of the collar portion 126E, preferably by securing a helically-shaped, relatively thin rod 156 to longitudinally adjacent bights of the collar portion 126E such as by welding, as indicated by reference numeral 157. As mentioned above in connection with the picket 100D shown in FIG. 13, such threads in the picket 100E of FIG. 14 may alternately be cut or otherwise formed in the interior of the collar portion 126E in a variety of ways familiar to those skilled in the art (such as with watchmakers' or other precision taps or dies).

FIG. 15 illustrates an enlarged fragmentary view of adjacent bights of the collar portion 126D of the picket 100D shown in FIG. 13. As suggested above, the helical rod 156 used for forming the internal threads on the collar portion 126E shown in FIG. 14 can be secured to longitudinally adjacent bights by welding, in a manner similar to that depicted in detail in FIG. 15 for the externally threaded collar portion 126D.

FIGS. 16 through 21 relate to a dental application of the present invention, wherein a picket generally similar to those described above is used for anchoring osseointegrated dental prosthesis implants. In FIG. 16, a bone structure 170 of a patient's jaw is shown being drilled by a generally cylindrical, hollow drilling tool 171 for purposes of forming an opening or socket 172 around a core portion 173. In FIG. 17, the drilling tool 171 is removed and the core portion 173 is broken off or otherwise removed from the opening 172.

FIG. 18 shows the drilling tool 171 being reinserted into the opening 172 in the bone structure 170 for purposes of forming the remainder of the opening or socket 172. Once the drilling operation is completed and the drilling tool 171 is removed, the opening 172 includes a generally hollow, cylindrical outer socket portion 176 and a generally annular, cylindrical inner portion 177, as perhaps best seen in FIG. 19. The radial thickness of the annular inner portion 177 should be substantially equal to the thickness of the helical members of the picket anchor.

FIG. 19 also illustrates an exemplary dental anchoring picket 200 being inserted into the opening 172 formed in the bone structure 170. The picket 200 includes two or more helical members 201 and 202, preferably having tapered ends 203 and 204, similar to those corresponding portions of the exemplary pickets described above. The helical members 201 and 202 are disposed generally concentrically about a longitudinal axis and spaced radially therefrom, with a lower or inner portion of the helical members 201 and 202 having longitudinally adjacent bights 217 and 218, respectively, which are longitudinally spaced from one another to define an anchoring portion 220. The anchoring portion 220 is adapted to be received in the opening 172 in the bone structure 170 in an anchoring engagement with the bone generally adjacent the annular inner portion 177.

The longitudinally adjacent bights 223 and 224 of the helical members 201 and 202, respectively, are relatively tightly wound, preferably in engagement with one another and preferably longitudinally secured to one another to form a collar portion 226. As shown in FIG. 20, when the picket 200 is secured to the bone structure 170, the bights 217 and 218 of the anchoring portion 220 threadably engage the bone structure adjacent the annular inner portion 177 of the opening 172, and the collar portion 226 is received in the generally hollow cylindrical outer socket portion 176 of the opening 172. The collar portion 226 may optionally be provided with external threads, in a manner similar to that described above, such as by securing a relatively thin rod 252 to the exterior of the collar portion 226. Such external threads can be used to engage an internally threaded dental prosthesis, or can serve to further enhance the secure engagement of the picket 200 to the bone structure 170, within the socket or opening 172. Furthermore, the collar portion 226 is preferably provided with internal threads, such as by way of securing a relatively thin rod 256 to the interior of the collar portion 226. Such internal threads serve to threadably and securely engage an externally threaded dental prosthesis 258 having a threaded post or stud 259.

Preferably, the helical members 201 and 202 of the picket 200 shown in connection with FIGS. 16 through 20 are composed of titanium or a titanium-bearing material, which is believed to provide the resistance to corrosion necessary to a dental prosthesis anchoring application. Furthermore, it is believed that such titanium or tianium-bearing material avoids adverse effects on the bone structure 170, as well as having the requisite strength for such dental applications. In this regard, the rods 252 and 256 which form the external and internal threads, respectively, on the collar portion 226 are also preferably composed of titanium or a titanium-bearing material, and can be fixedly secured to the collar portion 226 such as by heliarc welding, laser welding, or other suitable means known to those skilled in the art.

Once the picket has been threadably and snugly secured to the bone structure 170 within the opening 172, the bone tissue adjacent the annular inner portion 177 of the opening 172 grows back together between the bights 217 and 218 of the anchoring portion 220. This provides a very secure anchoring interconnection between the picket 200 and the patient's bone structure, while substantially eliminating, or a least minimizing, the irreversible damage or adverse effects on the bone structure. Furthermore, it is believed that the bone structure will grow together around the longitudinally-spaced helical bights 217 and 218 of the anchoring portion 220 more quickly than with previously-known implantation devices, and the helically-shaped members 201 and 202 are believed to have increased ability to absorb shocks, in a manner similar to that of the root structure of a healthy tooth. In addition to the above, the collar portion 226 fits snugly in the hollow cylindrical outer portion 176 of the opening 172 and is believed to provide the requisite rigidity and stability to support the surrounding bone structure.

It is also believed that bone marrow or a bone marrow bearing material can optionally be injected into the opening 172, prior to insertion of the picket 200, in order to further enhance the re-growth of the bone structure.

FIG. 21 illustrates an alternate embodiment of the present invention for dental prosthesis applications, wherein a picket 200A is generally similar in function to the picket 200 illustrated in connection with FIGS. 16 through 20, except that the integral, tightly wound collar portion 226 is replaced by a solid, generally hollow and cylindrical collar portion 226A. The collar portion 226A has an internal bore 227 with internal threads 230 cut or otherwise formed therein, and can optionally include external threads 264 cut or otherwise formed on its exterior. As in connection with the picket 200 described above, both the helically shaped members 201A and 202A of the anchoring portion 220A, as well as the solid collar portion 226A are preferably composed of titanium or a titanium-bearing material and are secured to one another by heliarc welding, laser welding, or other suitable means known to those skilled in the art. In other respects, the dental anchoring picket 200A is generally similar to the picket 200 described above in connection with FIGS. 16 through 20.

The foregoing discussion discloses and describes exemplary embodiments of the present invention. One skilled in the art will readily recognize from such discussion, and from the accompanying drawings, that various changes, modifications and variations may be made therein without departing from the spirit and scope of the invention as defined in the following claims.

What is claimed is:

1. A picket for anchoring an object to an article, comprising: two helical members disposed generally concentrically about a longitudinal axis and spaced radially therefrom, said helical members having adjacent bights longitudinally spaced from one another to define an anchoring portion of said picket; a generally cylindrical collar portion fixed to said anchoring portion, said anchoring portion being adapted for anchoring engagement with said article, and said collar portion being adapted for interconnection with said object in order to anchor said object to said article; and securing means fixed to said collar portion for removably securing said object to said collar portion, said securing means including spring means for resiliently and deflectably securing said object to said collar portion.

2. A picket according to claim 6, wherein said collar portion has internal threads therein for threadable attachment of said object thereto.

3. A picket according to claim 1, wherein said collar portion has external threads thereon for threadable attachment of said object thereto.

4. A picket according to claim 1, further comprising a threaded fastener fixed to said collar portion for threadably interconnecting said object to said collar portion.

5. A picket for anchoring an object to an article, comprising: two helical members disposed generally concentrically about a longitudinal axis and spaced radially therefrom; said helical members having first adjacent bights longitudinally spaced from one another to define an anchoring portion of said picket; and second longitudinally adjacent bights fixedly interconnected with one another to define a collar portion of said picket, said anchoring portion being adapted for anchoring engagement with said article, and said collar portion being adapted for interconnection with said object in order to anchor said object to said article; and a third helical member fixed to the interior of said collar portion to define internal threads therein for threadable attachment of said object to said collar portion.

6. A picket according to claim 5, wherein said third helical member comprises a helical rod, said rod being thin relative to the thickness of said helical members, said rod being fixedly secured to both of said helical members along a substantial longitudinal length of said collar portion.

7. A picket according to claim 5, wherein said helical members are composed of a titanium-bearing material, said second adjacent bights being fixedly secured to one another along a substantial portion of said collar portion.

8. A picket for anchoring an object to an article, comprising: two helical members disposed generally concentrically about a longitudinal axis and spaced radially therefrom; said helical members having first adjacent bights longitudinally spaced from one another to define an anchoring portion of said picket; and second longitudinally adjacent bights fixedly interconnected with one another to define a collar portion of said picket, said anchoring portion being adapted for anchoring engagement with said article, and said collar portion being adapted for interconnection with said object in order to anchor said object to said article; and a third helical member fixedly secured to the exterior of said collar portion to define external threads thereon for threadable attachment of said object to said collar portion.

9. A picket according to claim 8, wherein said third helical member comprises a helical rod, said rod being thin relative to the thicknesses of said helical members, said rod being fixedly secured to both of said helical members along a substantial longitudinal length of said collar portion.

10. A picket according to claim 8, wherein said helical members are composed of a titanium-bearing material, said second adjacent bights being fixedly secured to one another along a substantial portion of said collar portion.

11. A picket for anchoring an object to an article, comprising: two helical members disposed generally concentrically about a longitudinal axis and spaced radially therefrom; said helical members having first adjacent bights longitudinally spaced from one another to define an anchoring portion of said picket; and second longitudinally adjacent bights fixedly interconnected with one another to define a collar portion of said picket, said anchoring portion being adapted for engagement with said article, and said collar portion being adapted for interconnection with said object in order to anchor said object to said article; and a helical titanium rod, said rod being thin relative to the thicknesses of said helical members and being fixedly secured to at least one of said helical members along a substantial longitudinal length of the interior of said collar portion to define internal threads in said collar portion, said helical members also being composed of a titanium-bearing material, said second adjacent bights being fixedly secured to one another along a substantial portion of said collar portion.

12. A picket for anchoring an object to an article, comprising: two helical members disposed generally concentrically about a longitudinal axis and spaced radially therefrom; said helical members having first adjacent bights longitudinally spaced from one another to define an anchoring portion of said picket; and second longitudinally adjacent bights fixedly interconnected with one another to define a collar portion of said picket, said anchoring portion being adapted for anchoring engagement with said article, and said collar portion being adapted for interconnection with said object in order to anchor said object to said article; and a helical titanium rod, said rod being thin relative to the thicknesses of said helical members and being fixedly secured to at least one of said helical members along a substantial longitudinal length of the exterior of said collar portion to define external threads on said collar portions, said helical members also being composed of a titanium-bearing material, said second adjacent bights being fixedly secured to one another along a substantial portion of said collar portion.

13. A picket for anchoring an object to an article, comprising: two helical members disposed generally concentrically about a longitudinal axis and spaced radially therefrom; said helical members having first adjacent bights longitudinally spaced from one another to define an anchoring portion of said picket; and second longitudinally adjacent bights fixedly interconnected with one another to define a collar portion of said picket, said anchoring portion being adapted for anchoring engagement with said article, and said collar portion being adapted for interconnection with said object in order to anchor said object to said article; and spring means fixedly interconnected with said collar portion, said spring means being adapted for interconnection with said object for resiliently and deflectably interconnecting said object to said collar portion.

14. A picket according to claim 13, further comprising a threaded fastener fixedly secured to said collar portion for threadably interconnecting said object to said collar portion.

15. A picket according to claim 13, further comprising securing means fixedly secured to said collar portion for removably securing said object to said collar portion.

16. A method for making a picket for anchoring an object to an article, said method comprising:
providing a pair of elongated members;
forming an anchoring portion of said picket adapted for anchoring engagement with said article by forming said elongated members into a double helical configuration spaced radially from a longitudinal axis, said helical members in said anchoring portion being formed with adjacent bights longitudinally spaced from one another;
forming a generally cylindrical collar portion of said picket for attachment with said object in a fixed interconnection with said anchoring portion, said collar-forming step including forming a portion of said members into a double helical configuration with longitudinally adjacent bights of said helical members in said collar portion longitudinally engaging one another, said anchoring and collar portions being integrally formed with one another said helical members being composed of a titanium-bearing material, said collar-forming step further including welding adjacent bights of said helical members to one another in said collar portion; and forming internal threads on said cylindrical collar portion by providing a rod-like member having a thickness that is thin relative to the thicknesses of said helical members, and fixedly securing said rod-like member in a helical configuration along a substantial length of the interior of said collar portion to define internal threads therein.

17. A method for making a picket for anchoring an object to an article, said method comprising:
providing a pair of elongated members;
forming an anchoring portion of said picket adapted for anchoring enggagement with said article by forming said elongated members intoa double helical configuration spaced radially from a longitudinal axis, said helical members in said anchoring portion being formed with adjacent bights longitudinally spaced from one another;
forming a generally cylindrical collar portion of said picket for attachment with said object in a fixed interconnection with said anchoring portion, said collar-forming step including forming a portion of said members into a double helical configuration with longitudinally adjacent bights of said helical members in said collar portion longitudinally engaging one another, said anchoring and collar portions being integrally formed with one another, said helical members being composed of a titanium-bearing material, said collar-forming step further including welding adjacent bights of said helical members to one another in said collar portion; and
forming external threads on said cylindrical collar portion by providing a rod-like member having a thickness that is thin relative to the thicknesses of said helical members, and fixedly securing said rod-like member in a helical configuration along a substantial length of the interior of said collar portion to define external threads thereon.

* * * * *

UNITED STATES PATENT AND TRADEMARK OFFICE
CERTIFICATE OF CORRECTION

PATENT NO. : 4,738,062
DATED : April 19, 1988
INVENTOR(S) : Charles N. Dickey

It is certified that error appears in the above-identified patent and that said Letters Patent is hereby corrected as shown below:

On the Title Page Under "Other Publications"

Insert --Core-Vent Implant System - 1 pg.--.

Column 4, line 15, "secring" should be --securing--

Column 7, line 36, "tianium-bearing" should be --titanium-bearing--.

Column 8, line 47, Claim 2, "6" insert --1--.

Column 9, line 6, Claim 6, "thickness" should be --thicknesses--.

Column 10, line 64, Claim 16, after "and" insert new paragraph
   beginning with "forming".

Column 11, line 7, Claim 17, "enggagement" should be --engagement--.

Column 11, line 8, Claim 17, "intoa" should be --into a--.

Signed and Sealed this

Eleventh Day of October, 1988

Attest:

DONALD J. QUIGG

*Attesting Officer*      *Commissioner of Patents and Trademarks*